United States Patent [19]

Yasumoto et al.

[11] Patent Number: 5,138,053

[45] Date of Patent: Aug. 11, 1992

[54] METHOD FOR PRODUCING THIADIAZINE COMPOUNDS

[75] Inventors: Masahiko Yasumoto; Touru Tsuchiya; Yoichi Taguchi; Isao Shibuya; Katsumi Yonemoto, all of Tsukuba, Japan

[73] Assignee: Director-General of Agency of Industrial Science and Technology, Tokyo, Japan

[21] Appl. No.: 793,014

[22] Filed: Nov. 15, 1991

[30] Foreign Application Priority Data

Nov. 15, 1990 [JP] Japan ................................ 2-309250

[51] Int. Cl.$^5$ ............................................. C07D 285/34
[52] U.S. Cl. ........................................................ 544/8
[58] Field of Search .............................................. 544/8

[56] References Cited

U.S. PATENT DOCUMENTS

| | | | |
|---|---|---|---|
| 3,741,196 | 6/1973 | Chupp | 544/8 |
| 4,159,328 | 6/1979 | Ikeda et al. | 544/8 |
| 5,021,412 | 6/1991 | Nakaya et al. | 544/8 |

Primary Examiner—John M. Ford
Attorney, Agent, or Firm—Birch, Stewart, Kolasch & Birch

[57] ABSTRACT

There is disclosed a method for producing 2,6-bis(disubstituted amino)-1,3,5-thiadiazine-4-one compounds represented by formula (I). The method comprises reacting an N,N-disubstituted cyanamide represented by formula (II) with carbonyl sulfide represented by formula (III) under a high pressure. Formula (I)

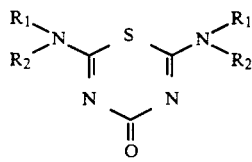

wherein $R_1$ and $R_2$ each represent an alkyl group or $R_1$ and $R_2$ may bond together to form a ring, Formula (II)

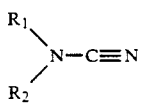

wherein $R_1$ and $R_2$ each have the same meanings as in formula (I), Formula (III)

S=C=O.

7 Claims, No Drawings

METHOD FOR PRODUCING THIADIAZINE COMPOUNDS

FIELD OF THE INVENTION

The present invention relates to a method for producing thiadiazine compounds, and particularly to a method for producing thiadiazine compounds using inexpensive raw materials by a one step reaction.

BACKGROUND OF THE INVENTION

It is known conventionally that many thiadiazine compounds have physiological activities; therefore they attract interest in the fields of medicine and agricultural chemicals. It is reported, for example, that some thiadiazine compounds have excellent pharmacological effects on inflammatory maladies and cardiopathies, and thiadiazine compounds have been recently developed as new type of vermin controller, such as buprofegin, that has a substituted amino group at 2-position of thiadiazine ring, and nematode controllers. However, the history of development of 1,3,5-thiadiazine compounds is short and synthesis examples are few, many of which involve complex steps and use expensive raw materials.

SUMMARY OF THE INVENTION

Therefore, an object of the present invention is to provide a method for preparing 1,3,5-thiadiazine compounds that become intermediates for medicines and agricultural chemicals using inexpensive raw materials by a one-step reaction in good yield.

Other and further objects, features, and advantages of the invention will appear more fully from the following description.

DETAILED DESCRIPTION OF THE INVENTION

The present method for the synthesis of thiadiazine compounds has advantages that the raw materials are readily available and a catalyst or the like is not required. Further, the product can be converted to a further compound (e.g., a cationic compound, such as thiadiazinium cation).

That is, the present invention provides a method for producing a 2,6-bis(disubstituted-amino)1,3,5-thiadiazine-4-one compound represented by the following formula (I), which comprises reacting an N,N-disubstituted cyanamide represented by the following formula (II) with carbonyl sulfide represented by the following formula (III): Formula (I)

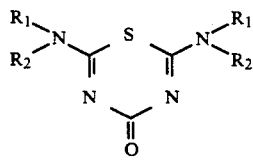

wherein $R_1$ and $R_2$ each represent an alkyl group or $R_1$ and $R_2$ may bond together to form a ring, Formula (II)

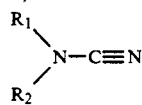

wherein $R_1$ and $R_2$ each have the same meaning in formula (I), Formula (III)

N,N-disubstituted cyanamides represented by formula (II) that are used as raw material in the present invention can be readily obtained, and desired substituents can be introduced by selecting the types of $R_1$ and $R_2$. Alkyl group represented by $R_1$ and $R_2$ is an alkyl group having preferably 1 to 8 carbon atoms, more preferably 1 to 4 carbon atoms, most preferably 1 to 3 carbon atoms. Alkyl groups represented by $R_1$ and $R_2$ include, for example, a methyl group, an ethyl group, and propyl group. When $R_1$ and $R_2$ bond together to form a ring, the ring is preferably a 3- to 8-membered ring, more preferably a 5- to 6-membered ring. Rings formed by bonding $R_1$ and $R_2$ include, for example, 1-pyrrolidine, 1-pyperidine, and 4-morpholine.

Carbonyl sulfide represented by formula (III) that is used as a raw material in the present preparation method is readily available. Although carbonyl sulfide is gas at normal temperatures and under normal pressures, it can be absorbed in a suitable solvent such as toluene and can be used in the form of a solution.

The N,N-disubstituted cyanamide and carbonyl sulfide are used in a molar ratio of 2:1 stoichiometrically, but generally the molar ratio selected is in the range of 1:10 to 10:1, preferably 3:1 to 1:3.

The present preparation method of this invention for producing compound of Formula (I) is performed under pressure. Although a higher pressure is preferable, generally the pressure selected is in the range of 1,000 to 12,000 atm. Although there is no particular restriction on the reaction temperature, the reaction temperature used is preferably in the range of 20° to 200° C., more preferably 80° to 160° C., so that side reactions such as thermal decomposition may be avoided. Reaction time in the present invention can be determined depending on the other conditions of reaction to be carried out, and usually it is preferably in the range of 2 to 50 hours, more preferably 2 to 30 hours, and most preferably 5 to 20 hours.

Now the present invention will be described in detail on the basis of Examples in detail. In the Examples, parts represent parts by weight and percentages related to yield are theoretical yields based on the raw material, N,N-disubstituted cyanamides.

EXAMPLE 1

7.7 parts of N,N-dimethylcyanamide and a solution of 5.5 parts of carbonyl sulfide absorbed in 104 parts of toluene were sealed in a Teflon (tradename of polyfluoroethylene, made by E. I. du Pont de Numoures & Co.) capsule (the raw material molar ratio=1:0.8), the capsule was placed in a high-pressure reaction tube, the pressure therein was increased to about 7,000 atm, the reaction tube was heated to a temperature of 130° C., and the pressure was further increased to 8,000 atm, which was maintained for 20 hours. Thereafter, the reaction tube was cooled to room temperature, and after the pressure was brought to normal pressure, the capsule was opened. The content was washed with hexane, and the obtained solid product was purified by recrystallizing from benzene, to yield 10 parts of the desired 2,6-bis(N,N-dimethylamino)1,3,5-thiadiazine-4-one (yield: 92%).

EXAMPLE 2

10.6 parts of 1-pyrrolidinecarbonitrile and a solution of 5.4 parts of carbonyl sulfide absorbed in 102 parts of toluene were sealed in a Teflon capsule (the raw material molar ratio=1:0.8), the capsule was subjected to 8,000 atm at 130° C. for 20 hours in a similar manner to Example 1, and separation was carried out similarly to Example 1, to yield 10.3 parts of the desired 2,6-bis(1-pyrrolidine)-1,3,5-thiadiazine-4-one (yield: 74%).

EXAMPLE 3

11.2 parts of 1-piperidinecarbonitrile and a solution of 5.4 parts of carbonyl sulfide absorbed in 102 parts of toluene were sealed in a Teflon capsule (the raw material molar ratio=1:0.8), the capsule was subjected to 8,000 atm at 160° C. for 20 hours in a similar manner to Example 1, and separation was carried out similarly to Example 1, to yield 11.3 parts of the desired 2,6-bis(1-piperidine)-1,3,5-thiadiazine-4-one (yield: 94%

EXAMPLE 4

12.5 parts of 4-morpholinecarbonitrile and a solution of 5.6 parts of carbonyl sulfide absorbed in 106 parts of toluene were sealed in a Teflon capsule (the raw material molar ratio=1:0.8), the capsule was subjected to 8,000 atm at 130° C. for 20 hours in a similar manner to Example 1, and separation was carried out similarly to Example 1, to yield 12.2 parts of the desired 2,6-bis(4-morpholine)-1,3,5-thiadiazine-4-one (yield: 77

EXAMPLE 5

7.7 parts of N,N-dimethylcyanamide and a solution of 5.5 parts of carbonyl sulfide absorbed in 104 parts of toluene were sealed in a Teflon capsule (the raw material molar ratio=1:0.8), the capsule was subjected to 4,000 atm at 130° C. for 20 hours in a similar manner to Example 1, and separation was carried out similarly to Example 1, to yield 3.6 parts of the desired 2,6-bis(N,N-dimethylamino)-1,3,5-thiadiazine-4-one (yield: 33%).

Having described our invention as related to the present embodiments, it is our intention that the invention not be limited by any of the details of the description, unless otherwise specified, but rather be construed broadly within its spirit and scope as set out in the accompanying claims.

What we claim is:

1. A method for producing 2,6-bis(disubstitutedamino)-1,3,5-thiadiazine-4-one compounds represented by the formula (I) shown below, which comprises reacting an N,N-disubstituted cyanamide represented by the formula (II) shown below with carbonyl sulfide represented by the formula (III) shown below under a high pressure: Formula (I)

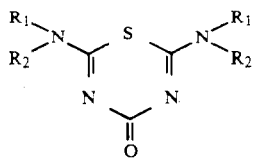

wherein $R_1$ and $R_2$ each represent an alkyl group or $R_1$ and $R_2$ may bond together to form a ring, Formula (II)

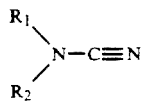

wherein $R_1$ and $R_2$ each have the same meanings as in formula (I), Formula (III)

$$S=C=O.$$

2. The method as claimed in claim 1, wherein the alkyl group represented by $R_1$ or $R_2$ is selected from the group consisting of alkyl groups having 1 to 8 carbon atoms.

3. The method as claimed in claim 1, wherein the alkyl group represented by $R_1$ or $R_2$ is selected from the group consisting of a methyl group, an ethyl group, and a propyl group.

4. The method as claimed in claim 1, wherein $R_1$ and $R_2$ bond together to form a 3- to 8-membered ring.

5. The method as claimed in claim 1, wherein the molar ratio of the N,N-disubstituted cyanamide and the carbonyl sulfide is in the range from 1:10 to 10:1.

6. The method as claimed in claim 1, wherein the reaction pressure is in the range from 1,000 to 12,000 atm.

7. The method as claimed in claim 1, wherein the reaction temperature is in the range from 20° C. to 200° C.

* * * * *